United States Patent
Lacey et al.

(10) Patent No.: US 7,135,687 B2
(45) Date of Patent: Nov. 14, 2006

(54) THERMOELECTRICALLY CONTROLLED X-RAY DETECTOR ARRAY STATEMENT REGARDING FEDERALLY SPONSORED RESEARCH

(75) Inventors: Joseph J. Lacey, Cambridge, WI (US); Lee F. Wichlacz, Menomonee Falls, WI (US); Douglas J. Snyder, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/716,367

(22) Filed: Nov. 18, 2003

(65) Prior Publication Data

US 2004/0071259 A1    Apr. 15, 2004

Related U.S. Application Data

(63) Continuation of application No. 10/064,609, filed on Jul. 30, 2002, now abandoned.

(51) Int. Cl.
- A61B 6/00 (2006.01)
- G01N 23/083 (2006.01)
- H05G 1/60 (2006.01)
- G01T 1/24 (2006.01)
- H01L 25/065 (2006.01)
- H01L 27/146 (2006.01)

(52) U.S. Cl. .......................... 250/370.15; 250/370.09; 378/4; 378/19

(58) Field of Classification Search ............. 250/336.1, 250/370.15, 238, 352, 339.03, 370.08–370.09, 250/370.11, 361 R, 336.01–363.02, 370.01; 378/4, 19, 127, 141, 199; 165/61, 253–4, 165/259, 9, 254

See application file for complete search history.

(56) References Cited

U.S. PATENT DOCUMENTS

| | | | | | |
|---|---|---|---|---|---|
| 4,150,552 | A | * | 4/1979 | Altman | 62/467 |
| 4,263,604 | A | * | 4/1981 | Jensen et al. | 257/188 |
| 4,283,817 | A | * | 8/1981 | Cotic | 445/35 |
| 4,639,883 | A | * | 1/1987 | Michaelis | 700/300 |
| 5,040,381 | A | * | 8/1991 | Hazen | 62/3.2 |

(Continued)

FOREIGN PATENT DOCUMENTS

JP    61201182 A  *  9/1986

(Continued)

OTHER PUBLICATIONS

"Designing with Thermoelectric Coolers". Thermal Design Guideline Paper [online]. Enertron, Inc., Dec. 5, 2001 [retrieved on Apr. 19, 2005]. Retrieved from the Internet: <URL: http://www.enertron-inc.com/pdf/Designing%20with%20Thermoelectric%20Coolers.pdf>.*

(Continued)

Primary Examiner—David Porta
Assistant Examiner—Frederick F. Rosenberger
(74) Attorney, Agent, or Firm—Quarles & Brady LLP

(57) ABSTRACT

Disclosed is an X-ray detector assembly for use in a computed tomography system. The X-ray detector assembly comprises an array of detector cells coupled between two rails. A thermoelectric cooler is coupled to an end of each of the rails, and is controlled to alternatively heat or cool the detector array to maintain the array in a substantially isothermal and thermally stable condition. The detector assembly preferably includes both passive and active cooling devices and insulation materials for controlling the temperature of the detector assembly. An electrical heater coupled at the center of the detector array can be used in conjunction with the TEC's to control the temperature profile of the detector array, and to minimize changes in the temperature gradients.

19 Claims, 7 Drawing Sheets

U.S. PATENT DOCUMENTS

| | | | | |
|---|---|---|---|---|
| 5,367,879 | A | * | 11/1994 | Doke et al. .................... 62/3.6 |
| 5,485,005 | A | * | 1/1996 | Aikens ................. 250/214 VT |
| 5,537,825 | A | * | 7/1996 | Ward ......................... 62/3.64 |
| 5,609,032 | A | * | 3/1997 | Bielinski ...................... 62/3.7 |
| 5,849,029 | A | * | 12/1998 | Eckhouse et al. ........... 607/104 |
| 5,970,113 | A | * | 10/1999 | Crawford et al. ............. 378/19 |
| 6,126,311 | A | * | 10/2000 | Schuh ......................... 374/21 |
| 6,230,497 | B1 | * | 5/2001 | Morris et al. ................. 62/3.7 |
| 6,249,563 | B1 | | 6/2001 | Snyder et al. |
| 6,370,881 | B1 | | 4/2002 | Maydanich |
| 6,411,672 | B1 | | 6/2002 | Sasaki et al. |
| 6,416,218 | B1 | | 7/2002 | Cheung |
| 6,459,757 | B1 | | 10/2002 | Lacey |
| 6,925,142 | B1 | * | 8/2005 | Pohan et al. ................... 378/19 |

FOREIGN PATENT DOCUMENTS

| | | | |
|---|---|---|---|
| JP | 10146332 A | * | 6/1998 |
| JP | 10 272130 A | | 10/1998 |

OTHER PUBLICATIONS

"Thermoelectric Reference Guide —Heat Sink Considerations". FerroTec, Inc., Oct. 22, 2003 [retrieved on Apr. 19, 2005]. Retrieved from the Internet: <URL: http://web.archive.org/web/20031022064230/http://www.ferrotec.com/usa/thermoelectric/ref/3ref5.htm>.*

Translation of Japanese Unexamined Patent Application (Kokai) Publication # 61-201182 A, Sep. 5, 1986 [translated Nov. 2004].*

* cited by examiner

THERMOELECTRICALLY CONTROLLED X-RAY DETECTOR ARRAY STATEMENT REGARDING FEDERALLY SPONSORED RESEARCH

CROSS-REFERENCE TO RELATED APPLICATIONS

This application is a continuation of U.S. Ser. No. 10/064,609, filed on Jul. 30, 2002, now abandoned.

STATEMENT REGARDING FEDERALLY SPONSORED RESEARCH

Not applicable.

BACKGROUND OF THE INVENTION

The present invention is generally directed to an X-ray detector array for use in a computed tomography system, and more particularly to a method and apparatus for maintaining an X-ray detector array in a substantially isothermal and thermally stable condition.

A computed tomography (CT) imaging system typically includes an x-ray source and an x-ray detector array mounted on opposite sides of a gantry with an imaging area interposed between. The detector array typically includes a plurality of detector elements arranged in rows and columns. The detector array or module includes the detection elements and associated electrical components to convert the x-ray signal to either a measurable analog or quantifiable digital signal. In many configurations the array is mounted to the gantry on axially separated rails.

In operation the x-ray source generates x-rays that are directed at the array. When an object (e.g., the torso of a patient) is positioned within the imaging area, x-rays passing through the object are attenuated to different degrees, the varying degrees of attenuation dependent upon characteristics of the material through which the x-rays pass within the imaging area (e.g., bone may attenuate to a greater degree than flesh, etc.).

In CT, the gantry is used to rotate the x-ray source and detector array about an object to be imaged so that data corresponding to every angle is collected. Thereafter, the collected data is filtered, weighted and typically back projected by an image processor to generate one or more diagnostic quality images.

In image reconstruction, it is assumed that the gain of each detector remains constant throughout a data acquisition process and that any change in x-ray signal intensity at the detector is due to patient anatomy. Unfortunately, this assumption is not 100% accurate for several reasons. One particularly acute source of error in this regard has to do with how detector element operation is affected by element conditions during operation. More specifically, as is the case with many different electronic components, detector element response to a specific stimuli (e.g., a specific intensity x-ray) varies as a function of temperature.

There are several ways in which temperature affects element output and overall accuracy of acquired data. First, not surprisingly, temperature directly affects element output (or gain) during operation, the module can be subjected to temperatures different than the calibration temperature, resulting in uncorrected gain errors. Second, temperature gradients along array rails and between rails has been known to cause thermal distortions in the mechanical structure leading to uncorrected gain errors. In one particular use, when the relative temperatures of the center and ends of the array vary over time, image artifacts can be introduced. Third, other detector array components (e.g., photo diode associated with detector elements), are also affected by changes in temperature. Specifically the shunt resistance of a photo diode drops exponentially with temperature which results in leakage currents and generally a decrease in the signal to noise ratio.

When array output varies as a function of element and array environment temperature, the quality of resulting images is adversely affected. To this end, it has been observed that temperature effects on array output sometimes result in image artifacts that adversely affect the diagnostic usefulness of the resulting images.

There are many sources of heat in CT systems that directly affect the temperature of the array. Specifically, the X-ray tube used to generate the X-ray beam generates a large amount of heat in a CT system. In addition, motors, processors and other CT system components generate heat in the vicinity of the array. In recent years, the desire to increase patient throughput (i.e., the number of acquisition sessions performed per day) has fueled the use of more powerful x-ray sources so that the amount of data required to generate images can be acquired in a shorter period of time. These higher powered systems, while appreciably faster than their predecessors, have only exacerbated the array heating problem and the associated image degradation.

To address temperature related array operation problems, the industry has developed various solutions aimed at maintaining nearly isothermal and thermal stable arrays. To this end, accepting that elements will heat during operation, most solutions provide some type of element heating configuration that is mounted with the array on the rails. The heating configuration is generally used to heat the elements approximately to an expected high temperature level and to maintain that temperature level throughout an acquisition period. The heater control point is set to be consistent with the expected high temperature limit and the maximum allowable module temperature change.

Unfortunately, in high power systems the array temperature can exceed the temperature at which acceptable image quality is achieved. Under these circumstances, a heating control cannot maintain the detector array within an acceptable operational temperature.

There remains a need, therefore, for a simple and economic method for maintaining a detector array at a constant temperature, and particularly for maintaining a detector array at a constant temperature when operated in conjunction with high-powered X-ray tubes wherein the highest temperature is greater than what is permitted by the imaging system.

SUMMARY OF THE INVENTION

An exemplary embodiment of the invention includes a detector array coupled between a set of rails. At least one thermoelectric cooler (TEC) is coupled to a distal end of the rails and a temperature sensor is coupled to the detector array to provide an indication of the actual array temperature. The TEC and temperature sensor are each coupled to a controller device which monitors the actual temperature and adjusts the power supply to the TEC to maintain a selected set point temperature. The controller device can command the TEC to switch between a "heat" mode and a "cool" mode, wherein the TEC facilitates either heating or cooling.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefor, to the claims herein for interpreting the scope of the invention.

DESCRIPTION OF THE PREFERRED EMBODIMENT

Figure 1:
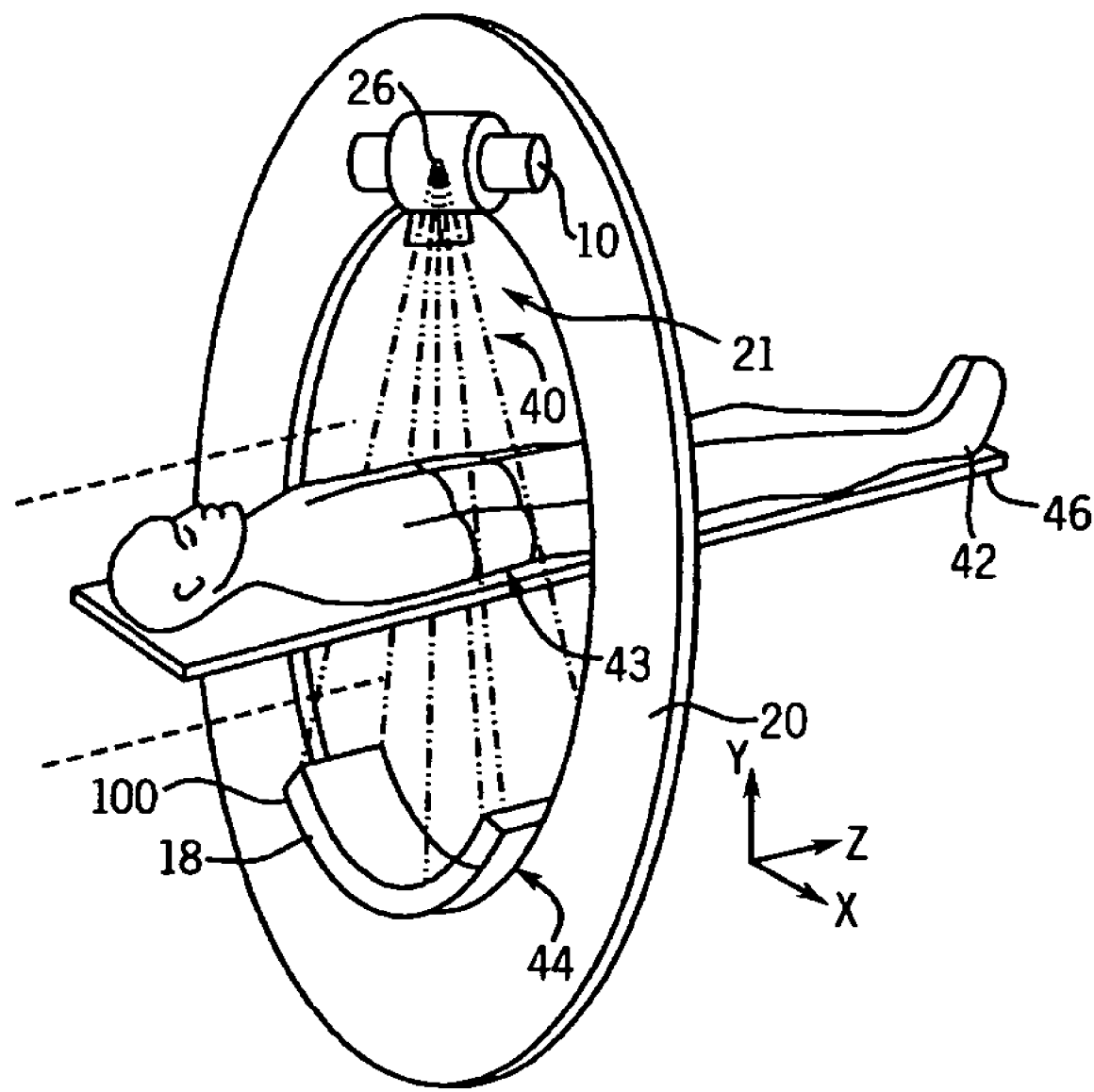
FIG. 1 is a perspective view of a CT apparatus used to practice the present invention which includes a detector array having rows and columns of detector elements and fan beam source.

Referring now to the Figures and more particularly to FIG. 1, a typical CT scanner for use in the present invention is shown. The CT scanner generally comprises a ring gantry 20 defining a central bore or imaging area 21. An X-ray source 10 is mounted opposite a detector assembly 44 on opposite sides of imaging area 21. The X-ray source 10 provides a fan beam of x-rays 40 that are directed at a portion 43 of a patient 42 resting on a support platform 46 to be scanned, and the detector assembly 44 receives the X-rays and provides intensity signals corresponding to the attenuation of the fan beam ray 40 as it passes through the object. This data is employed in image reconstruction to reconstruct one or more images of the object.

Figure 2:
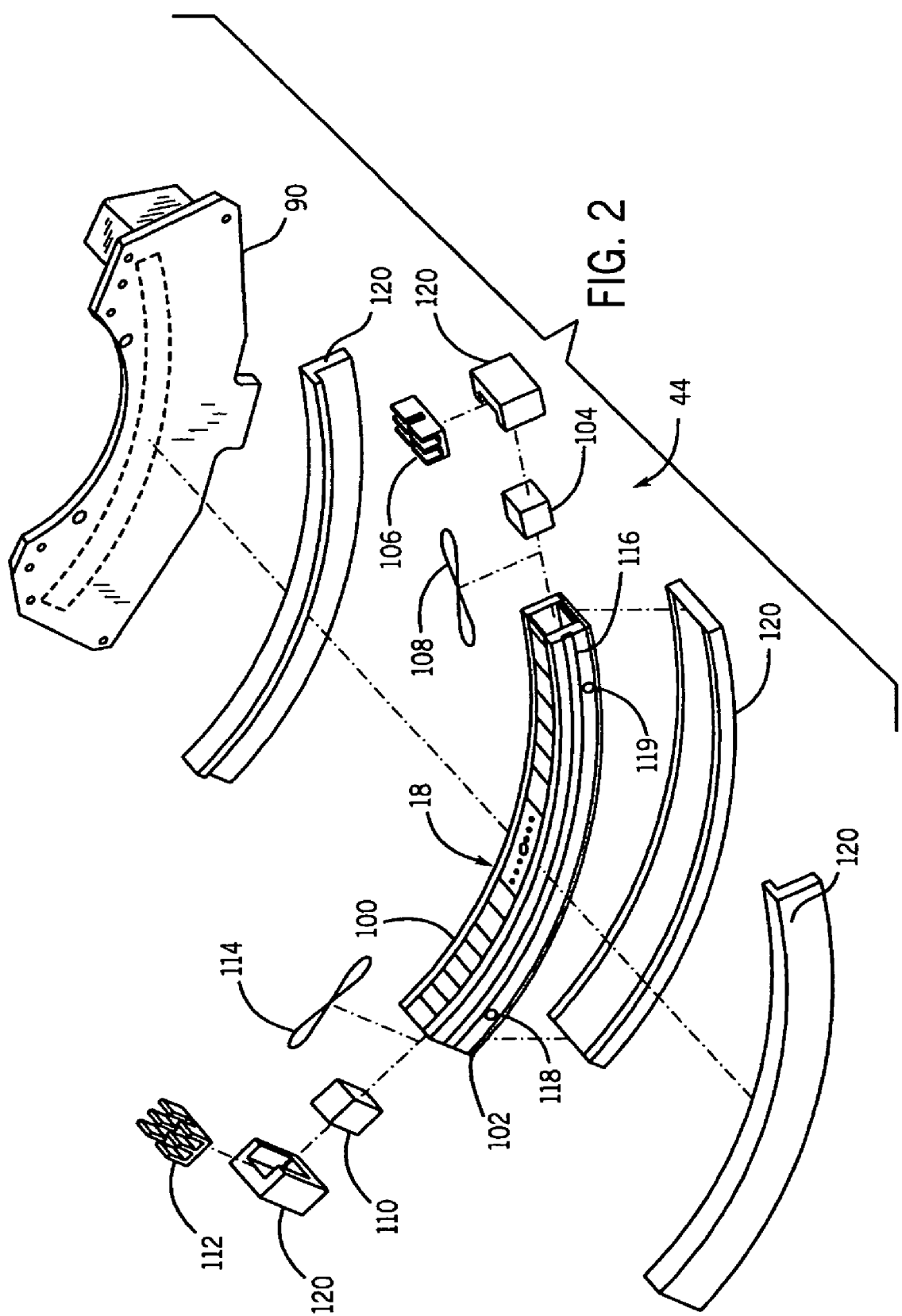
FIG. 2 is an exploded view of a detector assembly constructed in accordance with the present invention.
Figure 3:
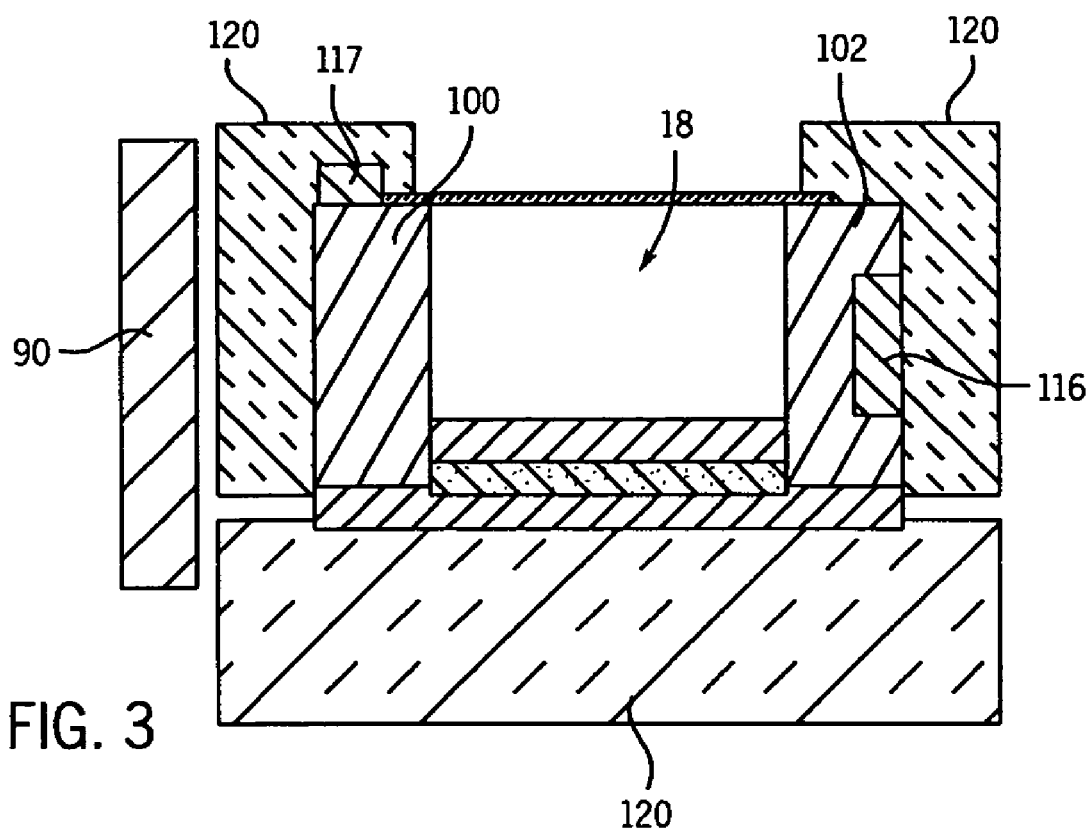
FIG. 3 is a cutaway side view of a detector assembly similar to the assembly of FIG. 2 in an assembled configuration.

Referring now to FIGS. 1, 2 and 3, detector assembly 44 is coupled to a mounting plate 90 which, in turn, is coupled to gantry 20 (see FIG. 1). Detector assembly 44 comprises an array of detector cells 18 coupled between first and second rails 100 and 102, respectively. Rails 100 and 102 are axially displaced along a Z or translation axis of the scanner system. Each of the detector elements 18 comprises a solid state X-ray detector as is described, for example, in commonly assigned U.S. Pat. No. 5,521,387, issued to Riedner et al. The detector elements 18 each receive x-rays and provides intensity measurements along separate rays of the fan beam 40. The detector elements 18 of the detector assembly 44 can be arranged in an arcuate configuration as shown, wherein a focal point 26 corresponds to a central point within the X-ray source. In some applications the detector assembly 44 may comprise a planar element. To facilitate detector assembly temperature monitoring, one or more temperature sensors 118 is embedded in detector assembly 44. Preferably, a temperature sensor 118 and a temperature sensor 119 are positioned at opposing ends of the detector array 44.

As best illustrated in FIG. 2, in the exemplary embodiment illustrated, first and second thermoelectric coolers (TEC) 104, 110, respectively, are coupled to opposite distal ends of detector assembly 44. TECs are solid state heat pumps that operate on the Peltier effect and can provide either heating or cooling to assembly 44. A typical TEC consists of an array of p and n-type semiconductor elements that act as two dissimilar conductors. The array of elements is typically soldered between two ceramic plates, electrically in series and thermally in parallel. As a DC current passes through one or more pairs of elements from n to the p-type semiconductor elements, there is a decrease in temperature at the junction ("cold side") formed by the two elements in the absorption of heat from the environment. The heat is carried through the TEC by electron transport and released on the opposite ("hot") side as the electrons move from a high energy state to a low energy state. The heat pumping capacity of a TEC is proportional to the current and the number of pairs of n and p-type elements, each pair typically referred to in TEC industry as a "couple". TECs useful in the present application are commercially available, such as the Thematec™ TEC series made by Melcor of Trenton, N.J.

Referring still to FIGS. 1 through 3, array 44 also includes several other components including insulation collectively identified by numeral 120 and two heat dissipating assemblies, a first dissipating assembly including a fan 108 and a heat sink 106 and a second assembly including a fan 114 and a heat sink 112. These components are described in more detail below.

Referring still to FIGS. 2 and 3, a high conductance insert 116 and 117 is coupled to each of rails 100 and 102. As illustrated, the inserts 116 and 117 can be provided along the sides of each rail 100 and 102 (e.g., see 116), or along a top edge of each rail 100 and 102 (e.g., see 117). The high conductance inserts 116, 117 are formed of a material selected to provide efficient heat transfer along the rails 100 and 102. The inserts 116 and 117 can be formed of, for example, a pyrolitic graphite (PG), copper, carbon based composite, or other material having a high thermal conductivity. Inserts 116 and 117 may also comprise a heat pipe such as that disclosed in U.S. Pat. No. 6,249,563, which is incorporated herein by reference for its description of a heat pipe device.

To dissipate heat produced by the TEC, a heat dissipation assembly comprising either a passive heat sink, an active heat dissipating device, or both, can be coupled to each of the thermoelectric coolers 104 and 110. As described above, in the exemplary embodiment, each of the first and second dissipating assemblies includes a fan 108, 114 and a sink 106 and 112, respectively. The sinks 106, 112, preferably comprise aluminum fins or any other suitable device known in the art. The fans 108, 114, or other active heat dissipation device, remove additional heat from the heat sinks 106, 112 while maintaining the distal ends of the detector array 44 at a relatively constant temperature.

Insulation 120 is provided on all sides of array 44 except for the array detecting side. The insulation minimizes heat transfer to the environment and thus renders a more efficient overall system. Also, advantageously, when in the cooling mode (i.e., when the array is to be cooled), the insulation 120 reduces cooling capacity requirements and also isolates the detector from environmental heat associated with other system components. Insulating material 120 can comprise any of a number of standard residential or commercial grade insulating materials such as Styrofoam, Fiberglass, neoprene foam, or may also comprise vacuum insulated panels (VIPs).

Figure 4:
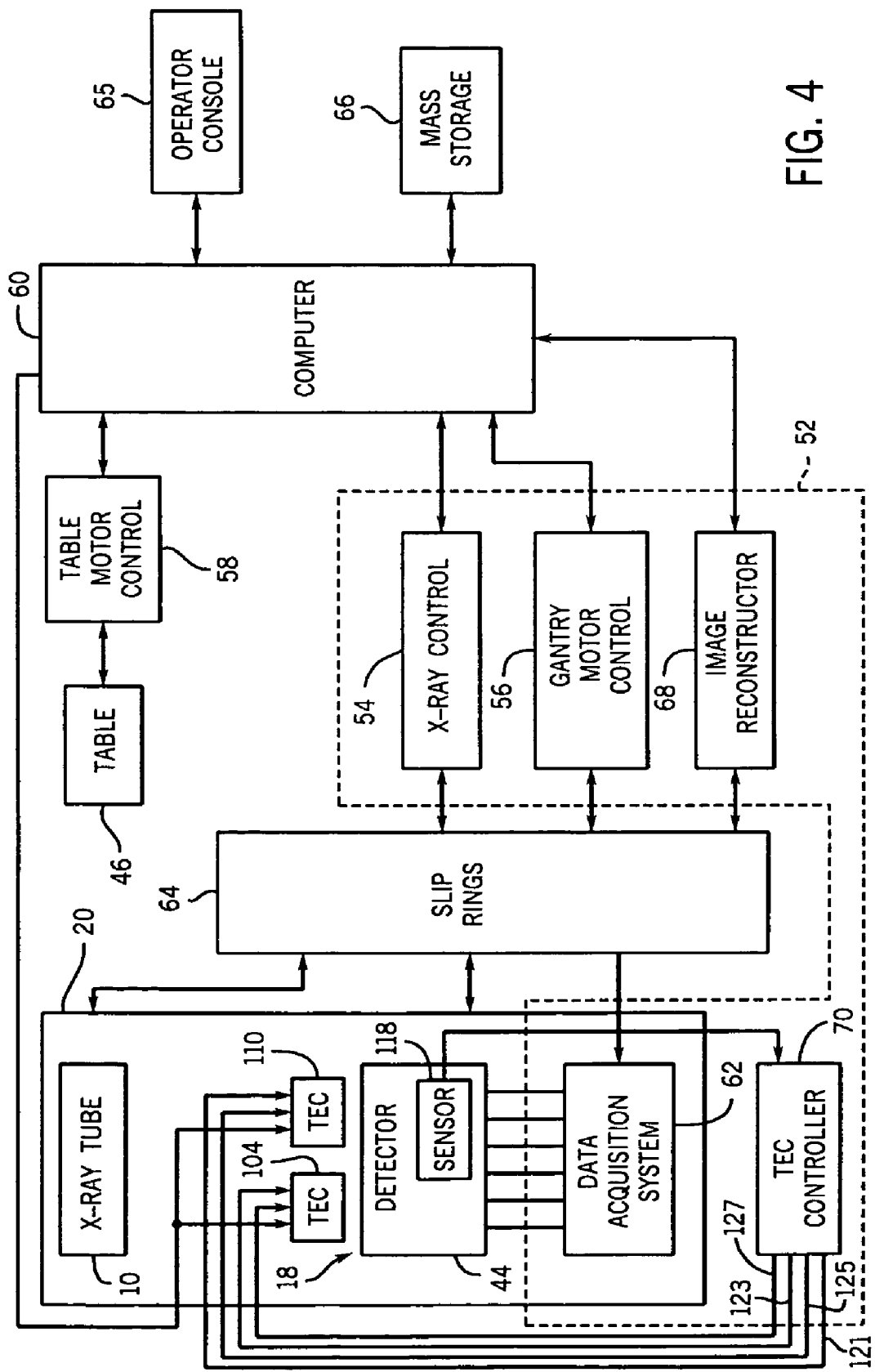
FIG. 4 is a block diagram of a CT control system which may be used to control the CT apparatus of FIG. 1 and which is useful for the purposes of practicing the present invention.

Referring now to FIG. 4, an exemplary control system for controlling the CT imaging system of FIG. 1 includes a table motor control 58, slip rings 64, a central processing computer 60, an operator's console 65, a mass storage device 66 and a plurality of control modules 52 associated with the gantry ring 20. The gantry control modules 52 include an x-ray control 54, a gantry motor control 56, a data acquisition system 62 and an image reconstructor 68. These modules are connected to the associated gantry via slip rings 64 and are linked to computer 60 for control purposes.

The gantry control modules 52 further include a TEC controller 70 for controlling TECs 104 and 110 to maintain the detector array 44 in a substantially isothermal and thermally stable condition. TEC controller 70 is preferably a commercially available device, such as the Themac™ TEC series produced by Melcor of Trenton, N.J. However, TEC controller 70 can comprise any number of devices capable of controlling TECs 104 and 110 using a control method such as a proportional integral derivative (PID) loop. TEC controller 70 is electrically coupled to one or more temperature sensor 118 in detector assembly 44, to each of TECs 104 and 110 by positive power supply lines 121 and 123, and negative power supply lines 125 and 127, respectively; and preferably to computer 60.

In operation an object, (e.g., patient 42 resting on movable table 46) is placed within imaging area 21. The X-ray source 10 provides an X-ray fan beam 40 which is directed at the patient 42. Gantry 20 is rotated around patient 42 and image data related to a volume 43 of the patient is collected. After passing through the patient 42 the X-rays of the fan beam 40 are received by array 44.

During data acquisition, TEC controller 70 maintains detector array 44 at a substantially constant temperature. A desired operational "set" point can be stored in memory, selected by a user through an interface coupled to the computer 60, established through the use of a potentiometer coupled to the TEC controller or in other ways known to those of skill in the art. The selected "set" point is provided to the TEC controller 70 via a control line. TEC controller 70 receives electrical signals from the temperature sensors 118 providing indications of the actual temperature of detector assembly 44 and compares the temperature values to the "set" point operational temperature provided by the computer 60. Based on the difference between the actual and desired temperatures, TEC controller 70 adjusts the output power supplied to the TECs 104 and 110. Although TECs 104 and 110 typically run in a "heating" mode, if the temperature of detector assembly 44 is higher than the desired operating temperature, TEC controller 70 can also switch the polarity of the power leads 121, 125 and 123, 127, respectively supplied to TECs 104 and 110. When the polarity of the power leads is reversed, the TECs provide a refrigeration function to cool the detector assembly 44 to the desired temperature. The cooling function is needed when the ambient temperature surrounding the CT scanner is significantly above the set point (beyond allowable module temperature change).

Figure 5:
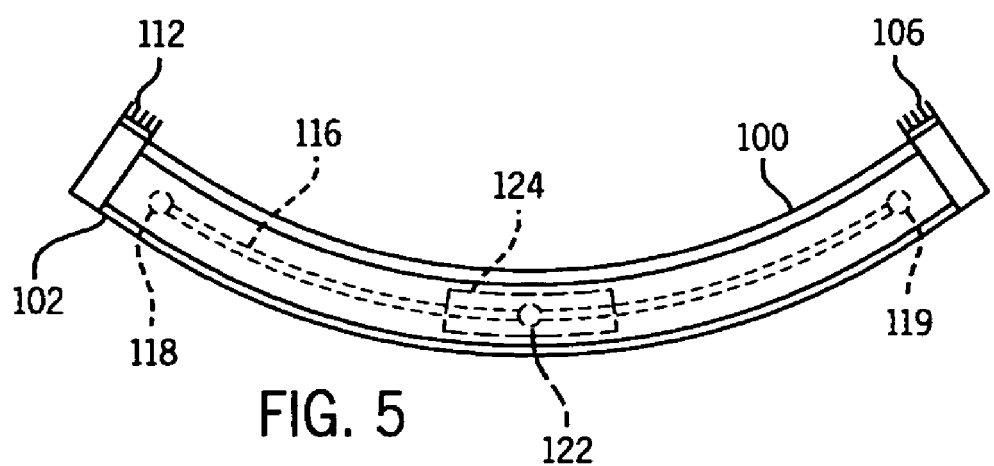
FIG. 5 is a side view of a detector assembly constructed in accordance with the present invention.

Referring now to FIG. 5, a second embodiment of a detector assembly 44 constructed in accordance with the present invention is shown. Here, a number of components are the same as those described with respect to FIG. 2, and these components are numbered in accordance with the description of FIG. 2. Other optional elements of FIG. 2 not illustrated in FIG. 5 could also be included. In particular the embodiment of FIG. 5 can also include the fan elements 108 and 114 and the insulated cover 120.

The embodiment of FIG. 5 includes a temperature sensor 122 provided in a center portion of the detector 44 along with an electric heater 124. The temperature sensor 122 and heater 124 are employed to monitor and regulate the distribution of heat on the center portion of the array, and operate in conjunction with the sensors 118 and 119 and TEC's 104 and 110 to maintain a selected temperature profile along the length of the detector assembly 44. The temperature profile is maintained such that, as the detector assembly 44 is moved from a cold environment to a hot environment, the relative temperature change between the center portion of the detector 44 and the distal ends remains constant. By maintaining the temperature profile along the detector 44, temperature-related mechanical shifting of the detector elements 18 is minimized or prevented, thereby minimizing the possibility of temperature induced image artifact.

Figure 6:
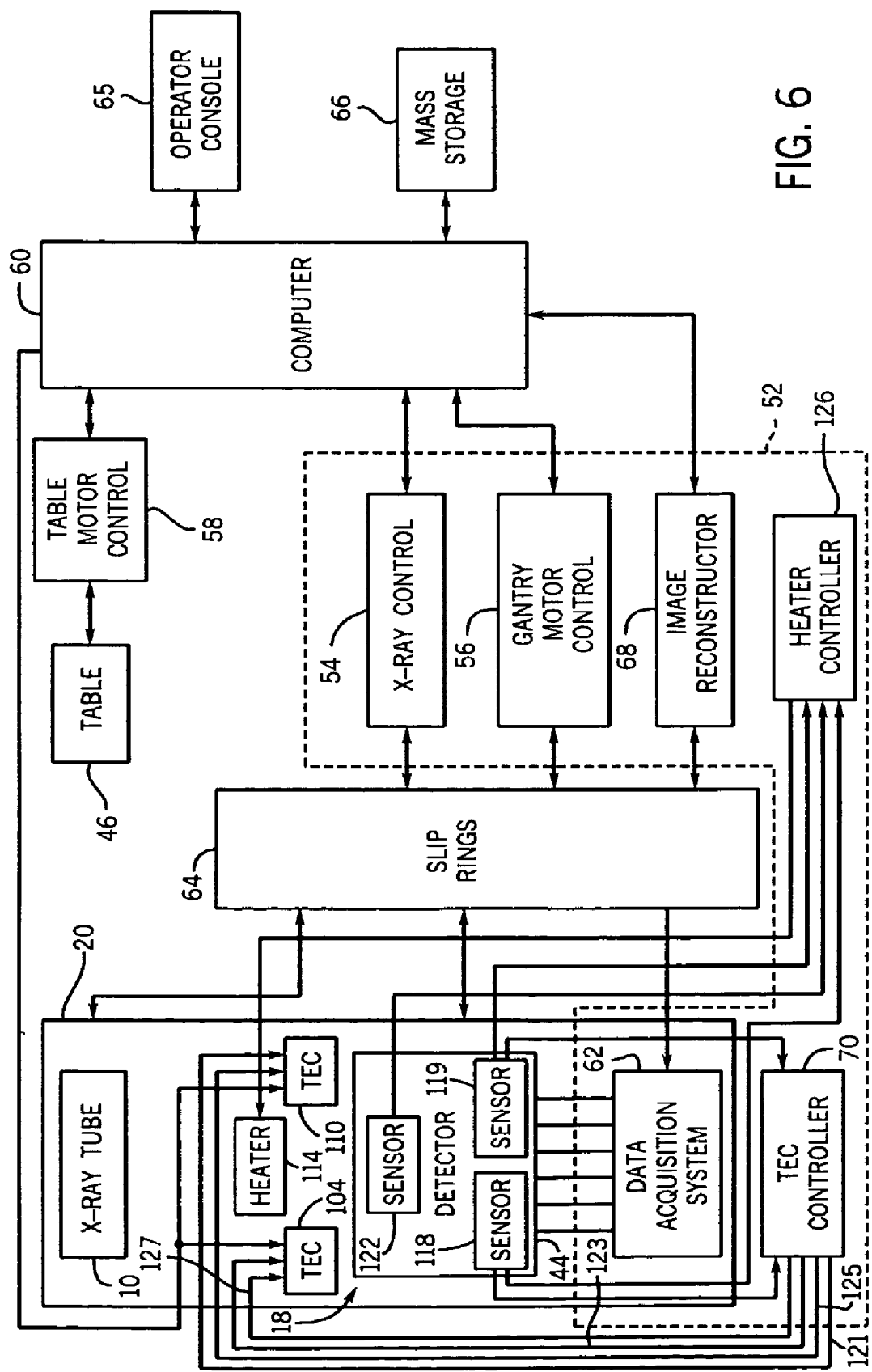
FIG. 6 is a block diagram of a CT control system which may be used to control the CT apparatus of FIG. 1 and the detector array of FIG. 5 and which is useful for the purposes of practice on the present invention.

Referring now to FIG. 6, a control system for operation in conjunction with the detector assembly 44 of FIG. 5 is shown. Again, in general the operation of the control system is similar to that of FIG. 4, and like components have been numbered accordingly. The control system includes a heater controller 126 which receives a sensed temperature signal from the sensor 122 and optionally from each of the sensors 118 and 119, thereby providing an indication of the temperature both at the center of the detector array 44 and at the opposing ends. Based on these sensed temperature values, the heater controller 126 drives the heater 124 and the TEC controller 70 drives the TECs 104 and 110 to maintain a selected temperature profile along the detector array 44, as described below.

Figure 7:
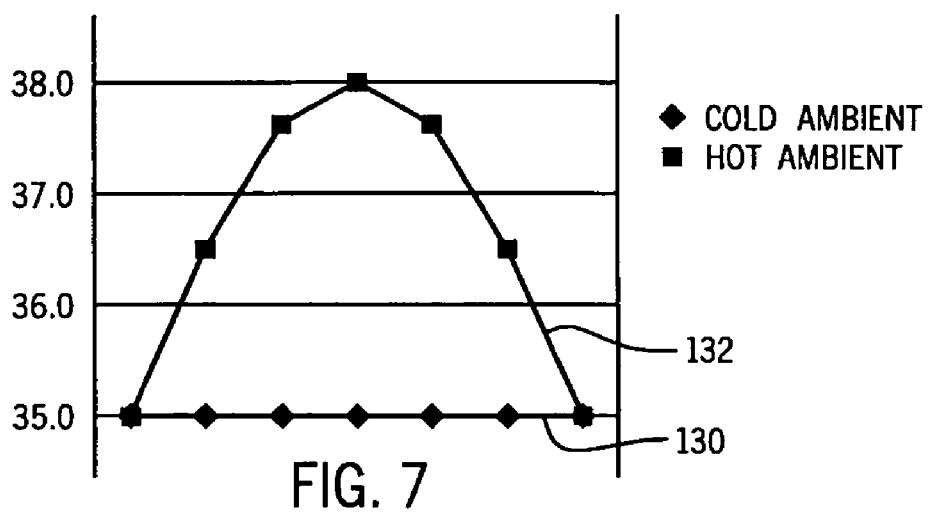
FIG. 7 is a chart illustrating the temperature profile along the detector array of FIG. 2 as operated in both a cold and a hot environment with a fixed temperature set point.
Figure 8:
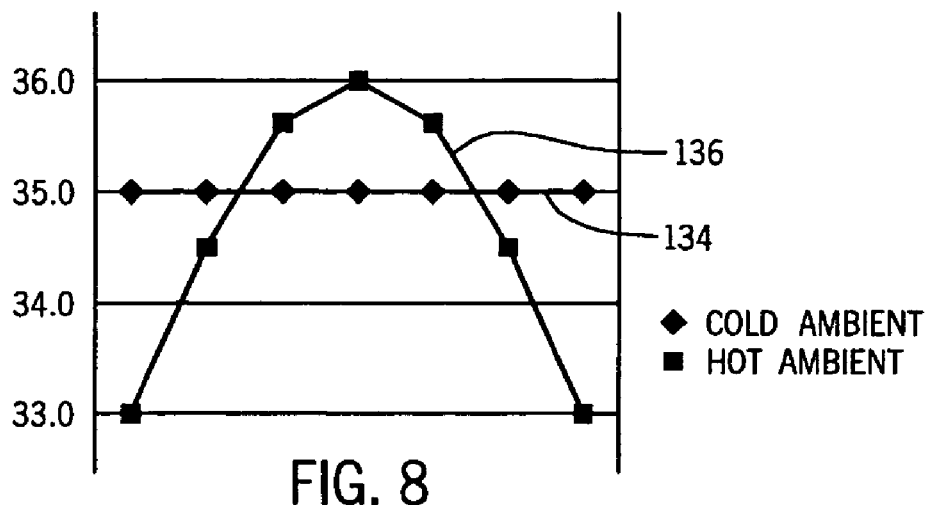
FIG. 8 is a chart illustrating the temperature profile along the detector array of FIG. 5 in both a cold and a hot environment as operated in accordance with a first control method.
Figure 9:
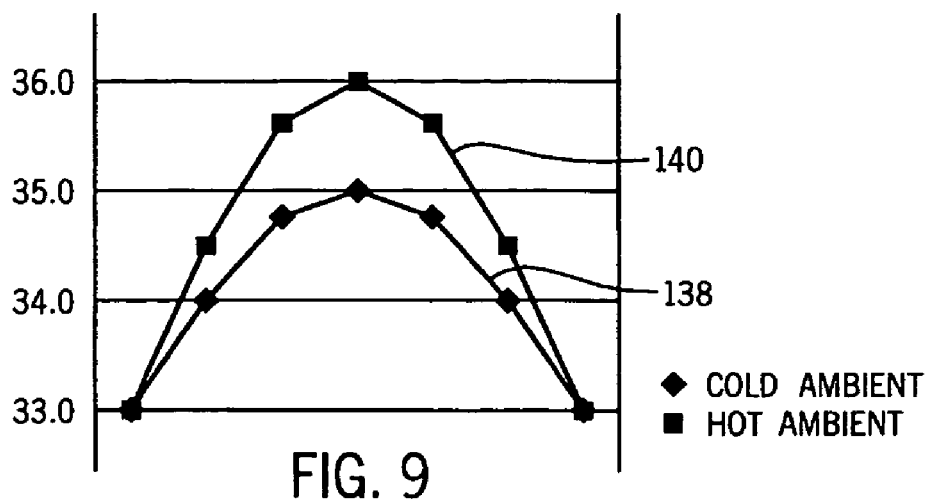
FIG. 9 is a chart illustrating the temperature profile along the detector array of FIG. 5 in both a cold and a hot environment as operated in accordance with a second control method.

Referring now to FIGS. 7, 8, and 9, temperature profiles illustrating the temperatures found along the length of an array 44 having a first control method, in which the temperatures of the distal ends of the array are monitored and controlled, and second and third control methods in which both the center portion and distal ends are temperature controlled, respectively, are shown. In all of these cases, it is desirable to operate the array 44 such that the temperature at the center portion of the array module 44 is maintained in a range between thirty and forty degrees Celsius, regardless of the surrounding environmental temperature, and to maintain the array below a selected maximum temperature. The following discussion centers on a region of interest between 30 and 40 degrees Celsius. For convenience, operation around a set point of thirty five degrees Celsius is assumed. Independent profiles are shown for each of a "hot" (about 45 degrees Celsius) and "cold" (about 25 degrees Celsius) environment. The TECs 104 and 110 can be used to heat and/or actively cool the detector array 44 in each of the described methods, and therefore can be used to cool the detector 44 to a temperature below the ambient air temperature surrounding the gantry.

Referring now specifically to FIG. 7, temperature profiles for a detector array 44 such as the detector array 44 of FIG. 2, are shown. In the detector array 44, the temperature set point is held constant at 35° C., as described above, and temperatures at the distal ends are monitored by sensors 118 and 119 and controlled by TECs 104 and 110 as described above. When operated in a cold environment, the temperature profile 130 of the detector array 44 is substantially isothermal, the temperature of the detector array 44 being held substantially at the selected set point of 35 degrees Celsius along the length of the array. When operated in a hot environment, the distal ends of the array 44 are maintained at the selected set point by the TECs 104 and 110, but the center portion rises to a temperature significantly higher than the selected set point, providing a parabolic temperature profile 132.

Figure 10:
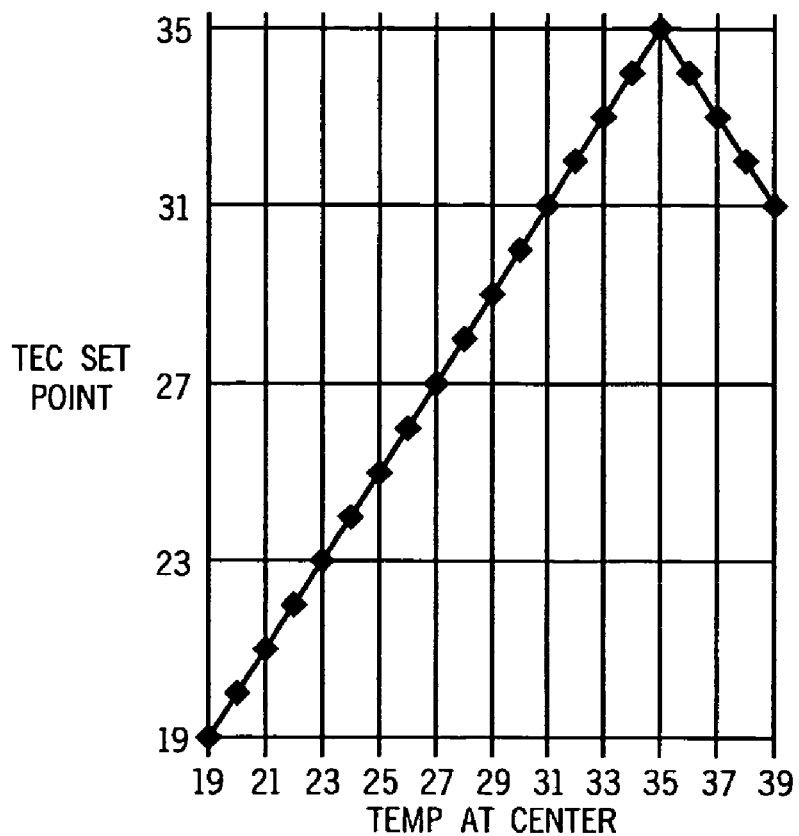
FIG. 10 is a chart illustrating the control method of FIG. 8.

Referring now to FIG. 8, temperature profiles for a detector array 44 such as the detector array of FIG. 5 operated in accordance with a first control method are shown. Here, the temperature of the center portion of the array 44 as detected by the sensor 122 is monitored, and the set point for control of the TEC's 104 and 110 is modified as a function of the temperature at the center portion. Referring now to FIG. 10, a graph illustrating the TEC set point versus temperature at the center portion is shown. Here, the TEC set point is continually raised at a predetermined slope until the selected operational temperature is reached at the center portion. As the temperature of the center portion increases, the TEC set point is dropped to lower the temperature of the array 44, thereby maintaining the temperature of the center portion at or near the selected operational set point and below the maximum level reacted in the prior art embodiment of FIG. 7. As a result, the cold environment temperature profile 134 of FIG. 8 is substantially isothermal, maintained at the selected operational temperature. In the hot environment temperature profile 136, however, the TEC's 104 and 110 are operated to maintain the distal ends at a lower temperature, thereby preventing the center portion from reaching the maximum temperature shown in FIG. 7. Here, therefore, the general parabolic profile of the hot environment detector array of FIG. 7 is maintained, but the distal ends and the center portion are each held at a lower temperature and nearer the set point than in the prior art system of FIG. 7.

Figure 11:
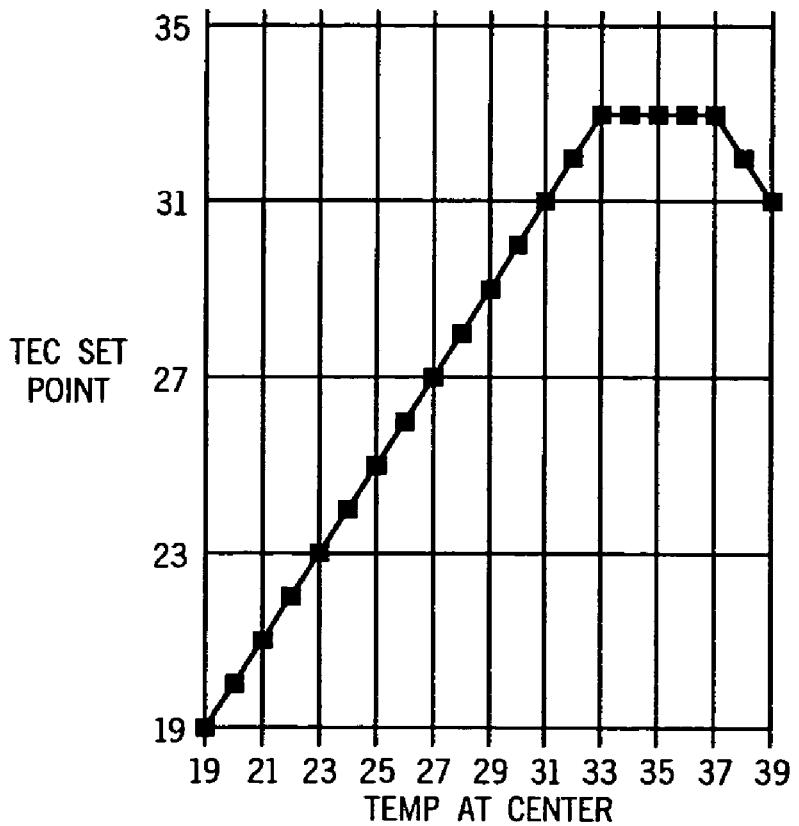
FIG. 11 is a chart illustrating the control method of FIG. 9.

Referring now to FIG. 9, temperature profiles for the detector array 44 of FIG. 5 as operated in accordance with a second control method are shown. Here, again, the temperature of the center portion of the array 44 as detected by the sensor 122 is monitored, and the set point for control of the TEC's 104 and 110 is modified as a function of this temperature. Referring now also to FIG. 11, again, the TEC set point is initially raised at a predetermined slope. Here, however, the TEC set point is selected to maintain the temperature at the distal ends of the detector array 44 lower than that of the temperature at the center portion of the detector array 44, regardless of whether the array 44 is operated in a hot or a cold environment. The TEC set point is maintained at a constant temperature level two degrees Celsius below the selected operational temperature in a selected range around the operational temperature, resulting in a cold environment temperature profile 138 which is parabolic, similar to the parabolic hot environment temperature profile 140. Because the general profile remains parabolic in both the hot and cold environments, thermal mechanical shifting of the array elements is limited, thereby minimizing temperature-induced noise in the acquired images.

It should be understood that the methods and apparatuses described above are only exemplary and do not limit the scope of the invention, and that various modifications could be made by those skilled in the art that would fall under the scope of the invention. For example, although the position of the sensors has been described at a center section and opposing ends of the detector assembly 44, the position and number of sensors can be varied to provide additional information regarding the temperature profile of the device to a controller. Furthermore, while specific control methods and temperature levels have been described, the control system of the present invention can be used to provide various temperature profiles in various temperature ranges by selectively controlling the application of the heater element 124 and applying the TEC devices 104 and 110 to heat or cool the detector array. To apprise the public of the scope of this invention, the following claims are made:

The invention claimed is:

1. A detector assembly for use in a computed tomography scanner, the detector assembly comprising:
   a detector array;
   a thermoelectric cooler coupled to the detector array;
   a temperature sensor coupled to the detector array;
   a heater, coupled to a center portion of the detector array;
   a controller device, the controller device being electrically coupled to the temperature sensor to receive an actual temperature signal and to the thermoelectric cooler to provide an adjustable power to the thermoelectric cooler, the controller device comparing the actual temperature signal to a set point value and adjusting the power supply to the thermoelectric cooler to selectively heat or cool the detector array and driving the heater to maintain the actual temperature substantially at the set point;
   wherein the controller drives the thermoelectric cooler and the heater to provide a selected nonuniform temperature profile along the array.

2. The detector assembly as defined in claim 1, wherein the selected nonuniform temperature profile along the array is substantially parabolic.

3. The detector assembly as defined in claim 1, further comprising a heat sink coupled to the thermoelectric cooler.

4. The detector assembly as defined in claim 3, further comprising:
   a first and second rail, the first and second rails being coupled to opposing sides of the detector array; and
   a conductive insert coupled to at least one of the first and second rails, the conductive insert transferring heat along the rail.

5. The detector assembly as defined in claim 4, wherein the conductive insert comprises at least one of a copper, a pyrolitic graphite, or a carbon based composite material.

6. The detector assembly as defined in claim 1, further comprising a fan directed at the thermoelectric cooler.

7. The detector assembly as defined in claim 1, further comprising an insulating cover, the insulating cover being coupled to each of the bottom, sides, and ends of the detector assembly.

8. A method for maintaining a temperature profile along a detector array in a thermally stable condition during CT scanning operations, the method comprising:
   coupling a thermoelectric cooler to each end of the detector array;
   selecting an operating temperature for operating the detector array;
   sensing an actual temperature of the detector array at each of a center portion and a first end or second end of the detector array;
   providing a heater to control the temperature of the center position of the array; and comparing the selected operating temperature and the actual sensed temperature, and commanding the thermoelectric cooler to heat or cool the detector array and the heater to heat the center portion of the array based on the difference between the selected operating and sensed temperatures, wherein a selected nonuniform temperature profile along a length of the detector is maintained.

9. The method as defined in claim 8, further comprising the step of coupling a heat conductive material along the length of the detector array, the heat conductive material transferring heat along the length of the detector array.

10. The method as defined in claim 8, further comprising the step of passively dissipating heat produced by the thermoelectric cooler.

11. The method as defined in claim 8, further comprising the step of actively dissipating heat produced by the thermoelectric cooler.

12. The method as defined in claim 8, further comprising the step of insulating the detector array to prevent heat produced by an X-ray tube or cold air in a gantry from affecting the detector assembly.

13. The detector assembly as defined in claim 8, wherein the selected nonuniform temperature profile along the array is substantially parabolic.

14. A detector assembly for use in a computed tomography scanner, the detector assembly comprising:
   a detector array;
   first and second rails, the first and second rails disposed on opposing sides of the detector array, each of the first and second rails including a conductive insert for conducting heat along the length of the detector array;
   a thermoelectric cooler coupled to a distal end of each of the first and second rails, the thermoelectric cooler including a positive and a negative power lead for receiving a power supply;
   a passive heat dissipating device coupled to the thermoelectric cooler;
   a plurality of temperature sensors coupled at spaced intervals along the detector array;
   a heater directed at a center portion of the detector array; and
   a controller device, the controller device being electrically coupled to the thermoelectric cooler, the heater, and to the plurality of temperature sensors, wherein the controller device receives a plurality of signals indicative of a temperature of the detector array from each of the temperature sensors, compares the received signals to a corresponding plurality of set point temperatures of a selected nonuniform temperature profile along the array and supplies a drive signal to each of the thermoelectric coolers and the heater to maintain the array at the selected nonuniform temperature profile along the array.

15. The detector assembly as defined in claim 14, further comprising an active heat dissipating device, the active heat dissipating device providing an air flow to the thermoelectric cooler to dissipate heat.

16. The detector assembly as defined in claim 14, wherein the thermoelectric cooler is coupled to the detector array to provide a heating element to the array.

17. The detector assembly as defined in claim 14, wherein the thermoelectric cooler selectively provides a heating element or a cooling element to the array.

18. The detector assembly as defined in claim 14, wherein the controller actively maintains the selected nonuniform temperature profile along the array such that the array is hotter in a center portion than at opposing ends of the array.

19. The detector assembly of claim 14, wherein the selected nonuniform temperature profile along the array is substantially parabolic.

* * * * *